United States Patent
Phillips et al.

(10) Patent No.: US 12,100,317 B2
(45) Date of Patent: Sep. 24, 2024

(54) SYSTEM AND METHOD TO OBJECTIVELY ASSESS ADOPTION TO ELECTRONIC MEDICAL RECORD SYSTEMS

(71) Applicant: CERNER INNOVATION, INC., Kansas City, KS (US)

(72) Inventors: Suchitra Joyce Phillips, Bengaluru (IN); Praveen Bhat Gurpur, Bengaluru (IN)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

(21) Appl. No.: 17/132,979

(22) Filed: Dec. 23, 2020

(65) Prior Publication Data

US 2022/0198953 A1 Jun. 23, 2022

(51) Int. Cl.
| | |
|---|---|
| G09B 7/08 | (2006.01) |
| G09B 19/00 | (2006.01) |
| G16H 10/20 | (2018.01) |
| G16H 10/60 | (2018.01) |
| G16H 40/20 | (2018.01) |

(52) U.S. Cl.
CPC ............ G09B 7/08 (2013.01); G09B 19/00 (2013.01); G16H 10/20 (2018.01); G16H 10/60 (2018.01); G16H 40/20 (2018.01)

(58) Field of Classification Search
CPC .......... G09B 7/08; G09B 19/00; G16H 10/20; G16H 10/60; G16H 40/20
See application file for complete search history.

(56) References Cited

U.S. PATENT DOCUMENTS

| | | | |
|---|---|---|---|
| 11,113,987 B1 * | 9/2021 | Jaggers | G09B 5/04 |
| 2011/0041077 A1 * | 2/2011 | Reiner | G06Q 30/02 |
| | | | 715/745 |
| 2012/0078660 A1 * | 3/2012 | Mangicaro | G16H 15/00 |
| | | | 705/3 |

(Continued)

OTHER PUBLICATIONS

Jung, So-Ra, "The perceived benefits of healthcare information technology adoption: construct and survey development" (2006). LSU Master's Theses. 816. Retrieved from Internet on Jul. 12, 2023: <https://digitalcommons.lsu.edu/gradschool_theses/816>. (Year: 2006).*

*Primary Examiner* — Kang Hu
*Assistant Examiner* — Correll T French
(74) *Attorney, Agent, or Firm* — Kraguljac Law Group, LLC

(57) ABSTRACT

Embodiments are disclosed herein for providing objective electronic medical record (EMR) system adoption analysis. In one embodiment subjective and objective inputs are received by a user via a user computing device. The subjective input includes at least one of knowledge of an EMR system, attitude towards the EMR system, or practice with the EMR system. The objective input includes demographic data related to the user of the EMR system. A score is then calculated for the objective and subjective input. Calculating the score includes weighting the objective and the subjective input to determine one or more of a knowledge score, an attitude score, or a practice score. It is determined that at least the attitude score is below a predetermined threshold. In response, an intervention module associated with attitude score is automatically transmitted to the user.

20 Claims, 14 Drawing Sheets

(56) References Cited

U.S. PATENT DOCUMENTS

| | | | |
|---|---|---|---|
| 2016/0042661 A1* | 2/2016 | Minkoff | G09B 7/00 |
| | | | 434/157 |
| 2016/0092658 A1* | 3/2016 | Leenaerts | G16H 10/20 |
| | | | 705/2 |
| 2016/0098805 A1* | 4/2016 | Vavroch | G06Q 40/125 |
| | | | 705/3 |
| 2016/0140857 A1* | 5/2016 | Jimenez | G09B 7/00 |
| | | | 434/219 |
| 2016/0225282 A1* | 8/2016 | Gordon | G09B 5/00 |
| 2018/0240140 A1* | 8/2018 | Whitley | G06Q 50/22 |
| 2019/0050774 A1* | 2/2019 | Divine | G16H 50/20 |
| 2021/0019803 A1* | 1/2021 | Khaderbad | G06Q 30/0203 |

\* cited by examiner

ADMINISTRATION AND INTERPRETATION

Scoring System: Calculate scores based on the value attributed in the response key

| Administration | Scoring System | Interpretation |
|---|---|---|
| Pre-intervention CLEAR Score | Facility-wise scoring | Analyze scores |
| Post-intervention | Role-wise scoring | Analyze trends |
| Consequent periodic administration CLEAR Score | Component-wise scoring | Impact of intervention |
| Spot administration | | |
| Intervention assessment | | |

FIG. 7

CLinical EMR Adoption Response (CLEAR) Score

Please answer the following questions in the spaces provided, circle or tick the most appropriate options.

Demographic and General Questions

1. Age _____

2. Gender ☐ Male ☐ Female

3. Name _____

4. How many years of experience have you had in this current job?

☐ <1 Year ☐ 1-2 Years
☐ 2-5 Years ☐ 5-10 Years
☐ >10 Years

5. What is your experience in healthcare?

☐ <1 Year ☐ 1-2 Years
☐ 2-5 Years ☐ 5-10 Years
☐ >10 Years

6. What is your highest education qualification?

_____

7. What is your role?

_____

8. What is the type of your Primary Health Center (PHC)

☐ Rural ☐ Urban

9. Computers usage

A. Have you used this Electronic Medical Record (EMR) System before?
☐ Yes ☐ No

B. Place of use

☐ Home ☐ Office/Hospital ☐ Both

C. Frequency of use

☐ Daily   ☐ Once a week   ☐ Rarely   ☐ Never

D. Have you received formal training in this EMR System?

☐ Yes  ☐ No

E. Have you handled clinical data on computers

☐ Yes  ☐ No

If yes;
☐ Inpatient  ☐ Outpatient  ☐ Research  ☐ Others (specify) _____

10. Was EMR training attended?   ☐ Yes  ☐ No

If yes;
When was the training attended (approximate)? _____ months back

Knowledge, Attitude, and Practice Questions:

1. Registration is done at:

☐ First visit  ☐ Every visit  ☐ Annually  ☐ Not sure  ☐ Don't know

2. Example of unique patient ID:

☐ Last name  ☐ Aadhar number  ☐ Age  ☐ Gender  ☐ Not sure  ☐ Don't know

3. Where can you modify patient's phone number
☐ Registration  ☐ Clinic application  ☐ Nursing station application  ☐ Back end application  ☐ Not sure  ☐ Don't know 4. System does not allow 2 patients to have the same phone number:
☐ Yes  ☐ No  ☐ Not sure  ☐ Don't know 5. Duplicate patient entries can cause
☐ Wrong data reported  ☐ Improper care  ☐ Both the above  ☐ None of the above  ☐ Not sure  ☐ Don't know 6. Medical errors occur due to
☐ Data on wrong patient  ☐ Missing demographic information
☐ Missing clinical data  ☐ All of the above
☐ Not sure  ☐ Don't know 7. Example of physician order entry is
☐ Hemoglobin level  ☐ Paracetamol syrup
☐ Antacid  ☐ All of the above
☐ Not sure  ☐ Don't know
8. Chief complaint is
☐ Diagnosis  ☐ Complaint that patient presents with
☐ History of patient  ☐ Not sure  ☐ Don't know

FIG. 9B

9. Example of substances that patients can be allergic to are
☐ Dust  ☐ Milk  ☐ Penicillin  ☐ All the above  ☐ Not sure  ☐ Don't know 10. Diagnosis cannot be changed once it is entered in the system     ☐ Yes  ☐ No  ☐ Not sure  ☐ Don't know 11. Choose the appropriate workflow ☐ Registration > Scheduling > Doctor consult      ☐ Doctor consult > Registration > Scheduling
☐ Scheduling > Doctor consult > Registration      ☐ All the above  ☐ Not sure  ☐ Don't know 12. Dispensing of drugs physically = completing of medicine order in EMR:

☐ Yes  ☐ No  ☐ Not sure  ☐ Don't know

13. Getting a blood draw in the lab = completing of lab order in EMR

☐ Yes  ☐ No  ☐ Not sure  ☐ Don't know

14. Can you add patient details such as address in the EMR after patient has seen the doctor
☐ Yes  ☐ No  ☐ Not sure  ☐ Don't know 15. Can all roles in the PHC use the same username and password ☐ Yes  ☐ No  ☐ Not sure  ☐ Don't know 16. Example of EMR report that is given to patient is:

☐ Visit Note  ☐ Registration card  ☐ Number of diabetics tested/day   ☐ All the above  ☐ Unsure  ☐ Don't know 17. MRN (Medical Record Number) is important because it is:

☐ Unique to patient   ☐ Traces record of patient   ☐ None of above   ☐ Both above reasons   ☐ Unsure  ☐ Don't know

18. Referral is:

☐ In-patient care  ☐ Providing patient with a visit note  ☐ Transfer of patient care to other facility
☐ Scheduling a visit  ☐ None of the above  ☐ Not sure  ☐ Don't know 19. Rate the following based on what you think on the below scale A. Regularly updating EMR systems reduces errors in the system ☐ Very important  ☐ Important  ☐ Not important  ☐ Useless B. Regularly updating EMR systems is necessary ☐ Very important  ☐ Important  ☐ Not important  ☐ Useless C. Patient demographics is necessary for physician's consult ☐ Very important  ☐ Important  ☐ Not important  ☐ Useless D. Identify the correct patient before treatment ☐ Very important  ☐ Important  ☐ Not important  ☐ Useless E. Being accurate in data capture during registration ☐ Very important  ☐ Important  ☐ Not important  ☐ Useless F. EMR use should be consistent (even at peak patient load)

☐ Very important  ☐ Important  ☐ Not important  ☐ Useless

G. All EMR systems should be updated regularly

☐ Very important  ☐ Important  ☐ Not important  ☐ Useless

H. Benefits of regularly updating EMR systems
☐ Very important  ☐ Important  ☐ Not important  ☐ Useless

I. EMR systems are used for
☐ Data entry ☐ Report generation ☐ Patient record ☐ Data analysis J. Updating EMR systems is time-consuming
☐ Yes ☐ No K. Preferred reasons for EMR system use
☐ Data is more secure ☐ Time saving ☐ Store more data ☐ Easy access to data ☐ Easy to write a report
☐ Not applicable L. Reasons for not using EMR
☐ Time consuming ☐ Difficult to use ☐ Lack of computer skill ☐ Electricity problems ☐ Duplication of records ☐ Not applicable 20. Tick the relevant answer A. EMR is used ☐ Daily (2)           ☐ Once a week (1)

☐ Once a month (1)    ☐ Not used (0)

B. In a day EMR is used

☐ Once a day (1)    ☐ For all patients (2)

☐ When patient load is less (1)    ☐ Not used (0)

C. Registration/Scheduling using EMR is done by

☐ All staff take turns (1)    ☐ Particular designated staff (2)

☐ Particular role - Pharmacist or Nurse (1)    ☐ Anyone who is free (0)

D. EMR Registration/Scheduling is done along with register entry

☐ Yes always (0)    ☐ Sometimes (1)

☐ Rarely (1)    ☐ Never (2)

E. Only first name and gender are enough for registration

☐ Yes(0)    ☐ No (2)

F. Back-up for electricity failure for EMR use

☐ Back-up generator (2)      ☐ Switch to paper system (0)

☐ Use paper and then transfer data in to EMR (1)      ☐ Wait for power to resume (0)

G. Back-up plan for internet downtime

☐ Use personal hotspots or a different provider (2)      ☐ Switch to paper system (0)

☐ Use paper and then transfer data in to EMR (1)      ☐ Wait for internet to resume (0)

H. Physician enters Diagnosis

☐ Always (2)      ☐ Sometimes (0)

☐ Never (0)

☐ Nurse / any other staff enters diagnosis on behalf of doctor (1)

I. Nurse / Doctor / Health worker who takes patient vitals (BP / Temp / SP02 etc)

☐ Simultaneously enters values in EMR (2)

☐ Writes the value on paper & immediately enters in EMR (1)

☐ Never enters in EMR (0)

☐ Writes the value on paper & later enters in EMR (1)

J. System to identify if the patient has completed the cycle within the clinic (for example registered patient goes away without seeing the physician ☐ Realtime (simultaneous) entries in EMR (2)

☐ All patients who have not taken medicines are marked as 'No Show' (0)

☐ No method to validate (0)

☐ Compare with paper registers and make entries in EMR (1)

Thank you for taking the time to complete this questionnaire!

FIG. 9F

SYSTEM AND METHOD TO OBJECTIVELY ASSESS ADOPTION TO ELECTRONIC MEDICAL RECORD SYSTEMS

BACKGROUND

Adoption and proper update of electronic medical record (EMR) systems is an essential part of the healthcare process. EMR systems are available to help streamline every aspect of the healthcare process to facilitate quick, efficient, and accurate process of patients. For instance, intake of a patient requires that large quantities of information be taken in and checked against current existing records which can be an incredibly time consuming and inefficient task without the use of an EMR system. Ensuring proper adoption to an EMR system, correct use of an EMR system, and appropriate update of an EMR system is integral to ensuring that the EMR and healthcare system is capable of functioning properly. At best, current healthcare processes may request that a user adopt to, and update an EMR system at given times, or send textual information regarding proper use of an EMR system. These can be ineffectual and ignored or forgotten about by a user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description and Drawings.

In brief and at a high level, embodiments of the present invention provide systems, methods, and computer-readable media for providing objective EMR system adoption analysis. Embodiments provide an application and/or cloud-based service that objectively analyzes electronic medical record (EMR) system adoption The objective adoption analysis system can determine the status of EMR system adoption based on the subjective input and the objective input from user groups and based on determining an EMR system has not been adopted, appropriate intervention measures can be instituted.

One aspect of the present disclosure relates to a computer-implemented method for providing objective EMR system adoption analysis. A subjective input and an objective input is received from a user via a user computing device. In aspects, the subjective input is comprised of at least one of a knowledge assessment related to an EMR system, an attitude assessment related to the EMR system, or a practice assessment related to the EMR system. In further aspects, the objective input comprises demographic data related to the user. In aspects, a score for the objective and subjective input is calculated, wherein calculating the score comprises applying a weight to the objective and the subjective input associated to determine one or more of a knowledge score, an attitude score, or a practice score. In further aspect, it is determined that at least one of the knowledge score, attitude score, or practice score is below at least one predetermined threshold. Based on determining that at least one of the knowledge score, attitude score, or practice score is below at least one predetermined threshold, it is determined that the user has not adopted the EMR system. In aspects, responsive to determining that the user has not adopted the EMR system, an intervention module associated with at least one of the knowledge score, attitude score, or practice score is automatically transmitted to the user.

In another aspect, the present disclosure relates to one or more non-transitory computer-storage media having computer-executable instructions embodied thereon that, when executed, perform a method of providing objective electronic medical record (EMR) system adoption analysis. In aspects, subjective and objective assessment is received by a user via a user computing device. In aspects, the subjective input is comprised of at least one of a user's knowledge of an EMR system, a user's attitude towards the EMR system, or a user's practice with the EMR system. In further aspects, the objective input comprises demographic data related to the user. In aspects, a score for the objective and subjective input is calculated, wherein calculating the score comprises applying a weight to the objective and the subjective input associated to determine one or more of a knowledge score, an attitude score, or a practice score. In further aspect, it is determined that at least one of the knowledge score, attitude score, or practice score is below at least one predetermined threshold. In aspects, responsive to determining that at least one of the knowledge score, attitude score, or practice score is below the at least one predetermined threshold, an intervention module associated with at least one of the knowledge score, attitude score, or practice score is automatically transmitted to the user. In further embodiments, a user group (either based on facility or role) is analyzed based on the inputs. An intervention module is administered that at least one of the knowledge score, attitude score, or practice score is below at least one predetermined threshold. After particular time intervals (3 months, 6 months, 12 months) the user group is re-assessed with the knowledge, attitude and practice assessments to determine positive or negative trend.

In yet another aspect, the present disclosure relates to a system for providing objective electronic medical record (EMR) system adoption analysis. The system includes a hardware processor configured to perform operations in response to receiving an instruction selected from a pre-defined native instruction set of codes and a memory. In aspects, the system further comprises an input component configured to receive, by a user, a subjective input and an objective input via a user computing device. In further aspects, the subjective input is comprised of at least one of a knowledge assessment related to an EMR system, an attitude assessment related to the EMR system, or a practice assessment related to the EMR system. In aspects, the objective input comprises demographic data related to the user. The system further comprises a calculation component configured to calculate a score for the objective and subjective input, wherein calculating the score comprises applying a weight to the objective and the subjective input to determine one or more of a knowledge score, an attitude score, or a practice score. The system is further comprised of an analysis component configured to determine that at least one of the knowledge score, attitude score, or practice score is below at least one predetermined threshold. The system is further comprised of an education component which is configured to automatically transmit, to the user, an intervention module associated with at least one of the knowledge score, attitude score, or practice score, responsive to determining that at least one of the knowledge score, attitude score, or practice score is below the at least one predetermined threshold.

BRIEF DESCRIPTION OF THE DRAWINGS

Embodiments are described in detail below with reference to the attached drawings figures, wherein:

FIG. 7 illustrates an exemplary scoring system for the objective electronic medical record (EMR) system adoption analysis, in accordance with an embodiment of the present disclosure.

FIGS. 9A-9F illustrate an example Assessment Questionnaire, in accordance with an embodiment of the present disclosure.

DETAILED DESCRIPTION

Figure 1A:
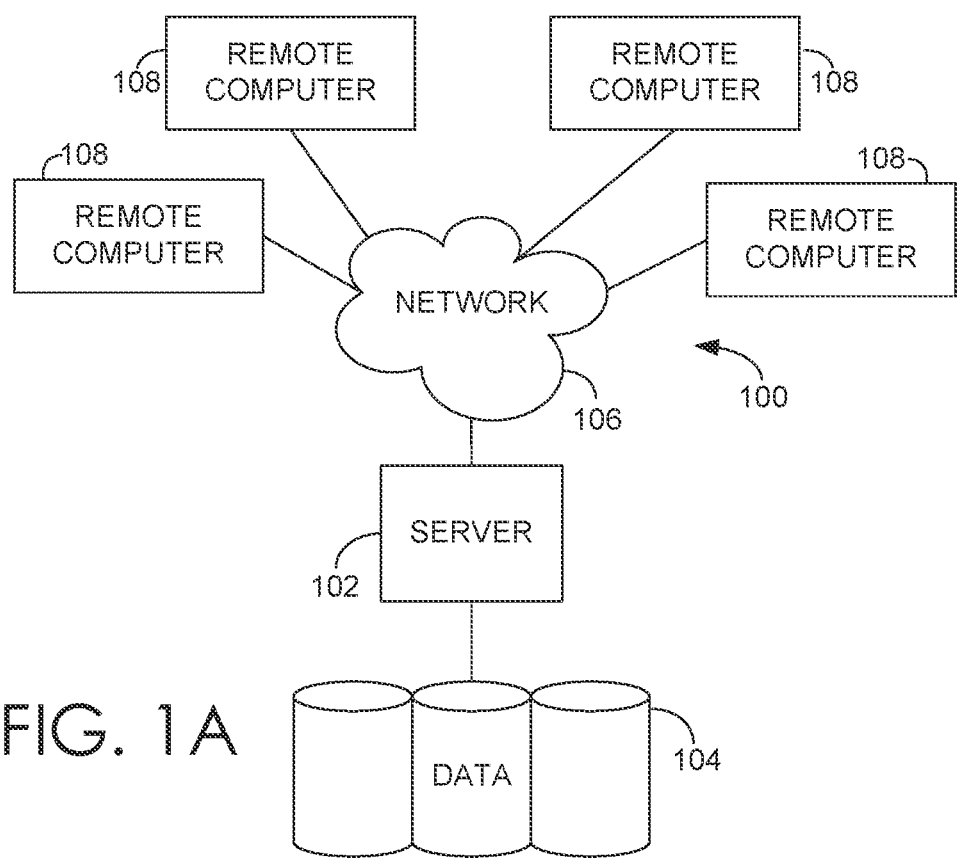
FIGS. 1A and 1B depict an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-useable instructions embodied on one or more computer-readable media, as discussed further herein.

At a high level, embodiments of the present invention provide providing objective EMR system adoption analysis. The software product can communicate with one or more disparate sources to, among other things, access data from, for example, an EMR (electronic medical record) system, store health data in an EMR system, identify one or more defects, generate one or more action items, and the like. The software product can provide the integration with an EMR system while preserving privacy of an individual and the data associated therewith accessed from the EMR system.

Embodiments herein provide a technological solution that addresses, solves, and overcomes the technological problems and/or shortcomings found in other implementations of EMR system adoption and update analysis. The solution herein objectively assesses the adoption and update of EMR systems. As EMR systems become more complicated and adopted by more users, the correct use and update of these systems is becoming paramount. A healthcare system whose users have not adopted well to an EMR system is incapable of utilizing its advantages. EMR systems have greatly increased the accuracy and efficiency of the healthcare process. Therefore ensuring that an EMR system has been properly adopted to is a necessity. Additionally, an EMR system which is not used properly cannot function properly, and the incorrect use of a system can impede processing power and misappropriate storage space. Proper adoption to the EMR system allows the system to work at peak efficiency and keeps the system from falling behind in updates. Ensuring proper adoption provides for less user error, increases processing power and frees up resources that otherwise would be devoted to remedying errors or improper use of the EMR system.

A computing environment is described with regard to the systems, methods, and computer-media described hereinabove. Turning to FIG. 1A, one example of a computing environment 100 is depicted, in accordance with an embodiment of the present invention. It will be understood by those of ordinary skill in the art that the computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1A. It will be appreciated by those having ordinary skill in the art that the connections illustrated in FIG. 1A are also exemplary as other methods, hardware, software, and devices for establishing a communications link between the components, devices, systems, and entities, as shown in FIG. 1A, may be utilized in implementation of the present invention. Although the connections are depicted using one or more solid lines, it will be understood by those having ordinary skill in the art that the connections of FIG. 1A may be hardwired or wireless, and may use intermediary components that have been omitted or not included in FIG. 1A for simplicity's sake. As such, the absence of components from FIG. 1A should be not be interpreted as limiting the present invention to exclude additional components and combination(s) of components. Moreover, though devices and components are represented in FIG. 1A as singular devices and components, it will be appreciated that some embodiments may include a plurality of the devices and components such that FIG. 1A should not be considered as limiting the number of a device or component.

Continuing, the computing environment 100 of FIG. 1A is illustrated as being a distributed environment where components and devices may be remote from one another and may perform separate tasks. The components and devices may communicate with one another and may be linked to each other using a network 106. The network 106 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 106, generally, provides the components and devices access to the Internet and web-based applications.

The computing environment 100 comprises a computing device 102 shown in the form of a server. Although illustrated as one component in FIG. 1A, the present invention may utilize a plurality of local servers and/or remote servers in the computing environment 100. The computing device 102 may include components such as a processing unit, internal system memory, and a suitable system bus for coupling to various components, including a data store, database, or data store/database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device 102 may include or may have access to computer-readable media. Computer-readable media can be any available media that may be accessed by computing device 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the computing device 102. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the computing device 102 uses logical connections to communicate with one or more remote computers 108 within the computing environment 100. In embodiments where the network 106 includes a wireless network, the computing device 102 may employ a modem to establish communications with the Internet, the computing device 102 may connect to the Internet using Wi-Fi or wireless access points, or the server may use a wireless network adapter to access the Internet. The computing device 102 engages in two-way communication with any or all of the components and devices illustrated in FIG. 1A, using the network 106. Accordingly, the computing device 102 may send data to and receive data from the remote computers 108 over the network 106.

Although illustrated as a single device, the remote computers 108 may include multiple computing devices. In an embodiment having a distributed network, the remote computers 108 may be located at one or more different geographic locations. In an embodiment where the remote computers 108 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 108 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 108 may be physically located in a non-medical setting, such as a packing and shipping facility or deployed within a fleet of delivery or courier vehicles.

Continuing, the computing environment 100 includes a data store 104. Although shown as a single component, the data store 104 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 104 includes physical memory that is configured to store information encoded in data. For example, the data store 104 may provide storage for computer-readable instructions, computer-executable instructions, data structures, data arrays, computer programs, applications, and other data that supports the functions and action to be undertaken using the computing environment 100 and components shown in exemplary FIG. 1A.

In various embodiments, the computing device 102, the one or more remote computers 108, and/or the data store 104 may be "sources" or "source devices," terms that are used interchangeably hereinafter. A source device can comprise any type of computing device capable of use by a user. By way of example and not limitation, a source device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a wearable electronic device with a camera (e.g., smart glasses, gesture-based wearable computers, etc.) a consumer electronic device, a workstation, or any combination of these delineated devices, a combination of these devices, or any other suitable computer device. The source device, as applied herein, can be utilized to access, for instance, the cloud-based solution to request creation of the item.

For example, one or more source devices may be an EMR server or any system that maintains, and provides access to, one or more EMR data store(s) containing records of treatment events, medication history, diagnoses, problems, allergies, demographic attributes, laboratory tests, time and date data, and any other health-related data, or any combination thereof for a plurality of patients. Additionally, the source devices can include clinical notes, appointment notes, records of issued prescriptions, diagnoses, care plans, bloodwork, urinalysis, treatment data, emergency contact information, and the like, for each patient of a healthcare facility or a plurality of healthcare facilities. Further, source devices can include images, representations, or clinical documentation of physical health data (e.g., X-rays, CT scans, ultrasound images, etc.). Additionally, in some embodiments, source devices can maintain one or more pharmaceutical formularies that identify prescriptions prescribed by, or available for prescription by, care providers.

In a computing environment having distributed components that are communicatively coupled via the network 106, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the computing device 102 may access, retrieve, communicate, receive, and update information stored in the data store 104, including program modules. Accordingly, the computing device 102 may execute, using a processor, computer instructions stored in the data store 104 in order to perform embodiments described herein.

Although internal components of the devices in FIG. 1A, such as the computing device 102, are not illustrated, those of ordinary skill in the art will appreciate that internal components and their interconnection are present in the devices of FIG. 1A. Accordingly, additional details concerning the internal construction device are not further disclosed herein.

It should also be understood that the computing environment 100 shown in FIG. 1A is an example of one suitable computing system architecture. Each of the components of FIG. 1A may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1A may be employed within the computing environment 100 within the scope of the present invention. Each may be implemented via a single device or multiple devices cooperating in a distributed environment. Additionally, other components not shown may also be included within the environment. As such, it should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Figure 1B:
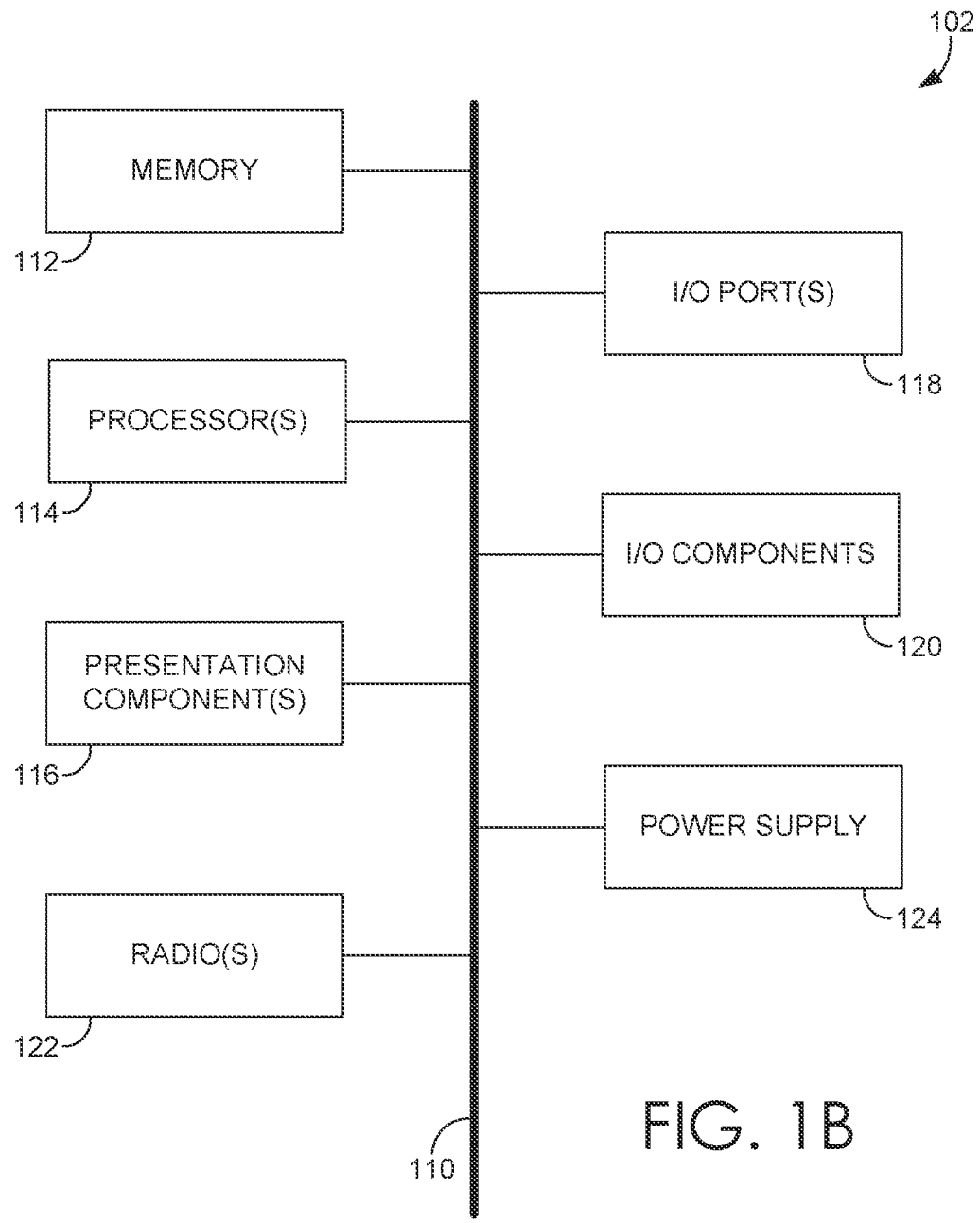

Turning to FIG. 1B, there is shown one example embodiment of the computing device 102. The computing device 102 includes a bus 110 that directly or indirectly couples one or more of the following components: memory 112, one or more processors 114, one or more presentation components 116, input/output (I/O) ports 118, input/output components 120, radio 122, and an illustrative power supply 124. Bus 196 represents what may be one or more buses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider the presentation components 116 to be an I/O component. Also, the one or more processors 114 may be coupled to and/or be integrated with the memory 112. As such, the diagram of FIG. 1B is merely one example of the computing device 102 that can be used in connection with one or more embodiments of the present invention. Distinction is not made between such categories as "workstation," "server," "laptop," "hand-held device," etc., as all are contemplated within the scope of FIG. 1B and reference to "computing device."

The computing device 102 includes a variety of computer-readable media, in embodiments. Computer-readable media can be any available media that can be accessed by the computing device 102 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 112 includes computer-storage media in the form of volatile and/or nonvolatile memory. The memory 112 may be removable, non-removable, or a combination thereof. Examples of hardware components for memory include solid-state memory, hard drives, optical-disc drives, etc. The computing device 102 may include the one or more processors 114 that read data from the memory 112 and/or the I/O components 120. The presentation component(s) 116 present data indications to a user or other device. An example of the presentation component(s) 116 include a display device, speaker, printing component, vibrating component, etc.

In some embodiments, the computing device 102 may include one or more radio(s) 122 that facilitates communication with a wireless network. Illustrative wireless telecommunications technologies include CDMA, GPRS, TDMA, GSM, and the like, though embodiments are not limited to telecommunications networks. The radio(s) 122 may additionally or alternatively facilitate other types of wireless communications including Wi-Fi, WiMAX, LTE, or other VoIP communications. As can be appreciated, in various embodiments, the one or more radio(s) 122 can be configured to support multiple technologies and/or multiple radios can be utilized to support multiple technologies.

I/O ports 118 allow the computing device 102 to be logically coupled to other components, including I/O components 120, some of which may be built in to the computing device 102. Illustrative components include a microphone, joystick, game pad, satellite dish, scanner, printer, wireless device, etc. The I/O components 120 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 102. The computing device 102 may be equipped with depth cameras, such as stereoscopic camera systems, infrared camera systems, RGB camera systems, touchscreen technology, and combinations of these, for gesture detection and recognition. Additionally, the computing device 102 may be equipped with accelerometers or gyroscopes that enable detection of motion. Finally, the computing device 102 depicted in FIG. 1B is provided as one example of any number of suitable computers.

The computing device 102 may actually be a plurality of computing devices, in some embodiments. In various embodiments, the computing device 102 may include one or more software agents, an adaptive multi-agent operating system, or the like. It will be appreciated that the computing device 102 may take the form of an adaptive single agent system or a non-agent system, for example. The computing device 102 may be a distributed computing system of multiple remote computers, a data processing system, a centralized computing system, a networked computing system, or alternatively, may be a single computer such as a desktop or laptop computer.

Figure 2:
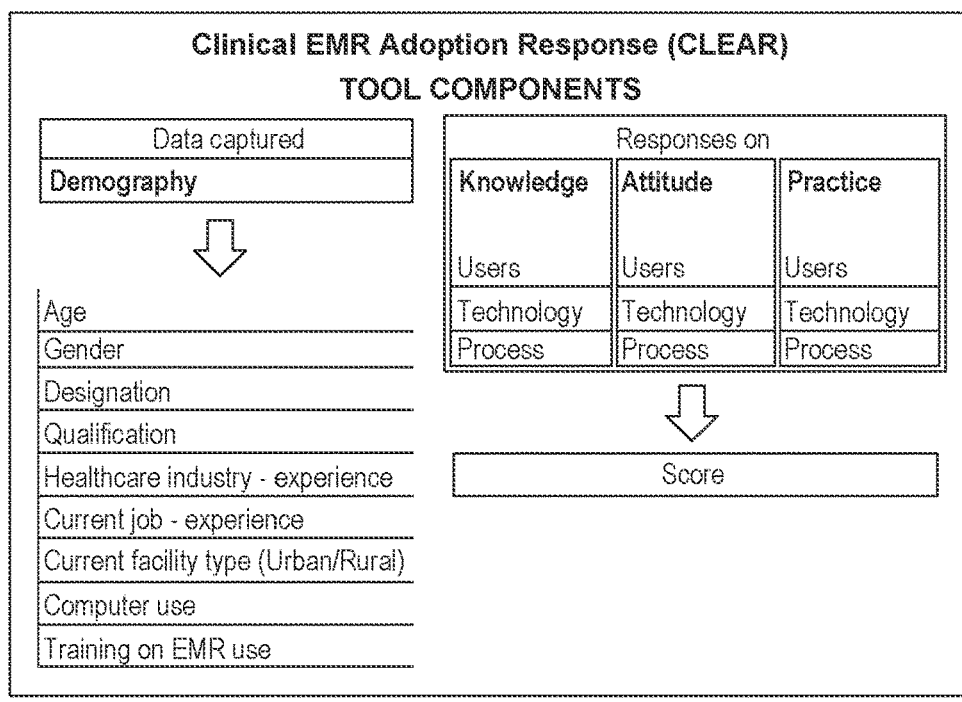
FIG. 2 illustrates tool components of an exemplary embodiment, in accordance with an embodiment of the present disclosure.

Turning to FIG. 2, a diagram of exemplary tool components of an exemplary embodiment of the disclosure. In example embodiments, the method for providing objective electronic medical record (EMR) system adoption analysis, may also be described as the Clinical EMR Adoption Response, or CLEAR system. In further embodiments, the CLEAR system has tool components 200 comprised of a data capture tool. In example embodiments, the data capture tool is capable of capturing demographic data associated with age, gender, designation, qualification, experience within the healthcare industry, experience in a current job position, whether their current facility is an urban or rural facility, the amount of experience a user has with computer use, a user's amount of training on EMR system, among others. In example embodiments, this data can be automatically determined based on data associated with a user which is stored in an associated computer system. In further embodiments, the data is captured through user input, wherein a user manually enters the data via a graphical user interface. In further embodiments, the tool components 200 comprise a response tool. In example embodiments, the response tool is capable of receiving response related to knowledge related to users, a technology, or a process associated with an EMR system. In further embodiments, the response tool is capable of receiving response related to attitude related to users, a technology, or a process associated with an EMR system. In further embodiments, the response tool is capable of receiving response related to practice related to users, a technology, or a process associated with an EMR system.

In example embodiments, the tool components are configured to analyze the received information to determine a score. In example embodiments, the data capture tool may receive or retrieve demographic data and generate a score for a user based on the received or retrieved demographic data. In further embodiments, the response tool may receive response data and generate a score for a user based on the received response data. In further embodiments, the tool components 200 are configured to work together. In example embodiments, a score can be determined based on both the received or retrieved data from the data capture tool, and the received response data. As will be discussed throughout, this determined score may be used to determine at least that an EMR system is not downloaded, or that an EMR system is not updated. In further embodiments, the score may be used objectively to determine how a user, facility, group, is adapting to and incorporating EMR systems.

Figure 3:
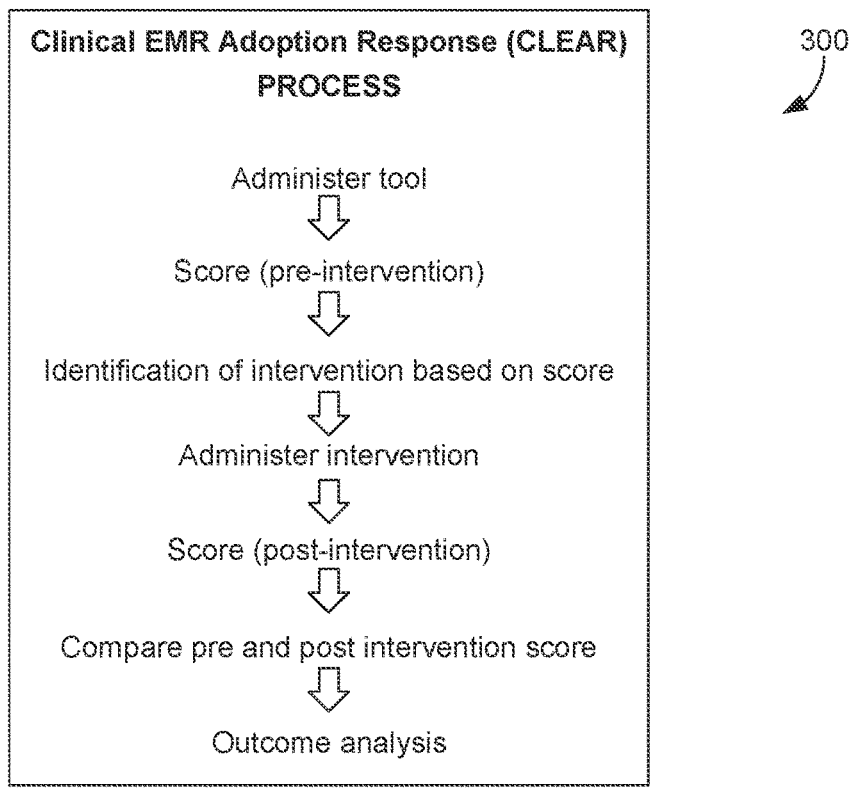
FIG. 3 illustrates an example process administration and intervention, in accordance with an embodiment of the present disclosure.

Turning to FIG. 3, an example process 300 for the CLEAR system is provided, in accordance with an embodiment of the present disclosure. In example embodiments, the process 300 may include the steps of administering the tool components 200, scoring the retrieved or received data, identifying at least one intervention based on the score, administering at least one intervention, reassessing the score after administering the intervention, compare the pre-intervention and post-intervention scores, and analyzing the outcome to determine the effectiveness of the intervention. In example embodiments, this process may be run multiple times. In further embodiments, if the analysis of the outcome determines that the intervention was ineffective, the tool may be re-administered and the process started again. In example embodiments, the outcome analysis may be stored in an associated database such that the retrieved and received data, the score, the intervention, and the outcome are all stored in association with one another. In example embodiments, this allows the process to be more effective by identifying effective and ineffective interventions. Analyses of the assessments may be at a user group level (based on role, facility, age, years of experience).

Based on the levels of score and if below the predetermined threshold, the user group will be subjected to an intervention module (also referred to herein as a "retraining module") after which a re-administration and re-assessment of the CLEAR score is carried out.

Figure 4:
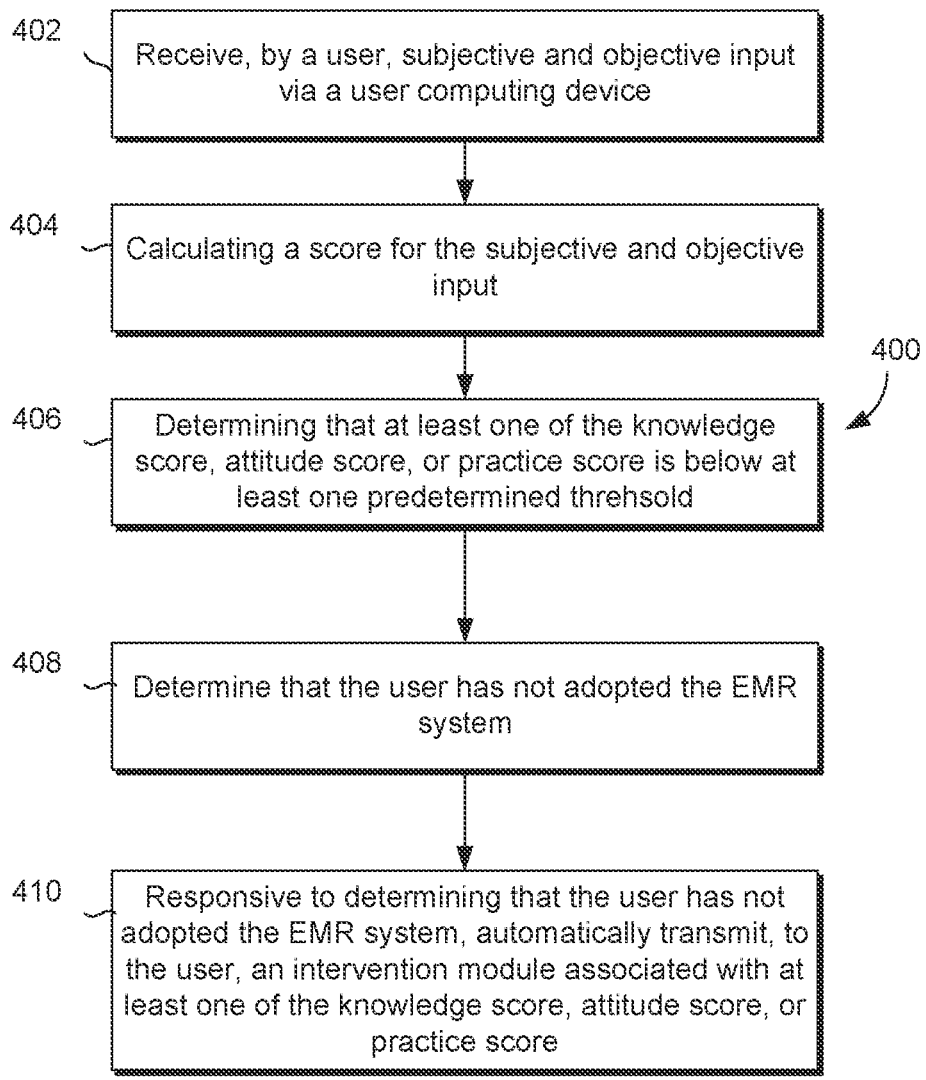
FIG. 4 illustrates a flow diagram of a computer-implemented method for providing objective electronic medical record (EMR) system adoption analysis, in accordance with an embodiment of the present disclosure.

Turning to FIG. 4, a flow diagram of computer-implemented method for providing objective electronic medical record (EMR) system adoption analysis is illustrated. In example embodiments, at step 402, a subjective input and an objective input are received by a user via a computing device. In further embodiments, the input is received via a graphical user interface associated with the computing device. The subjective input may be comprised of at least one of a knowledge assessment related to an EMR system, an attitude assessment related to the EMR system, or a practice assessment related to the EMR system.

In further embodiments, the knowledge assessment may be comprised of questions related to a user's understanding of different aspects of an EMR system, or updates to an EMR system. In example embodiments, the attitude assessment may be comprised of questions related to a user's attitude towards an EMR system or an EMR system update. These questions may be designed to determine what a user thinks of an EMR system or an update to an EMR systems, for example, how important they believe it is for healthcare systems to implement. In example embodiments, the practice assessment may be comprised of questions related to a user's understanding of how often an EMR system is used, or how often an EMR system should be updated. Additionally, this may comprise questions related to when it is appropriate to use an EMR system, or who should use different aspects of an EMR system. Additionally, the objective input may be comprised of demographic data related to the user. Example questions related to both the objective inputs and subjective inputs are illustrated in FIG. 9.

In example embodiments, the subjective input may be received via the selection of icons associated with a graphical user interface. In further embodiments, the subjective inputs may be received as text or audio data in association with prompts displayed on a graphical user interface. In example embodiments, the objective input may be retrieved from a user computer. For example, the objective input may be retrieved from a database associated with a user. In further examples, the objective input may be retrieved from metadata associated with a user. In further embodiments, the subjective input and the objective input are analyzed by conducting natural language processing of the input. Based on analyzing the inputs using natural language processing, the subjective input is then categorized into at least one of the categories of knowledge, attitude, or practice. An example embodiment of a display associated with the input of objective and subjective data is illustrated in FIG. 9.

At step 404, a score is calculated for the subjective and objective input. Calculating the score may comprise applying a weight to the subjective and objective input to determine one or more of a knowledge score, an attitude score, or a practice score. In further embodiments, three separate scores may be determined, namely, a knowledge score, an attitude score, or a practice score. Each of the scores may be related to the difference between a received input, and the expected input. For example, each of the questions related to one of the assessments may have a correct answer or a correct range. Based on receiving an incorrect answer to an assessment, this may lower the score of the user for that particular assessment. At step 406, it is determined that at least one of the knowledge score, attitude score, or practice score is below at least one predetermined threshold.

At step 408, based on the knowledge, attitude and practice scores, it may be determined that the user has not adopted well to using the EMR system. In further embodiments, determining that the user has not adopted well to using the EMR system may require only a knowledge, attitude, or practice score, and in further embodiments, it may require that each of the assessments be provided and scored. In example embodiments, determining that the user has not adopted well to using the EMR system may require both the subjective input and the objective input. At step 410, responsive to determining that the user has not adopted the EMR system, an intervention module associated with at least one of the knowledge score, attitude score, or practice score is automatically transmitted to the user. In further embodiments, the method may comprise causing display of a notification on a second user device notifying that the intervention module has been transmitted to the first user.

In further embodiments the scores determined for the user may be used to determine a remedy for the user. For example, if the knowledge score for a particular user is below a threshold, but the attitude, and practice scores are above the threshold, the determined remedy may be associated with educating the user associated with the score. In additional examples, if the attitude score is below a threshold, the remedy may be comprised of training related to informing the user as to the importance of EMR systems. Additionally, if the practice score is below a threshold, the remedy may be comprised of intervention such as practical use retraining for the EMR system. Each of these embodiments may also include causing display on a graphical user interface, associated with the user device, a notification that the determined remedy is required. In further embodiments, this may also comprise causing display, on a graphical user interface of a second user device, a notification that the determined remedy is required for the first user.

Figure 5:
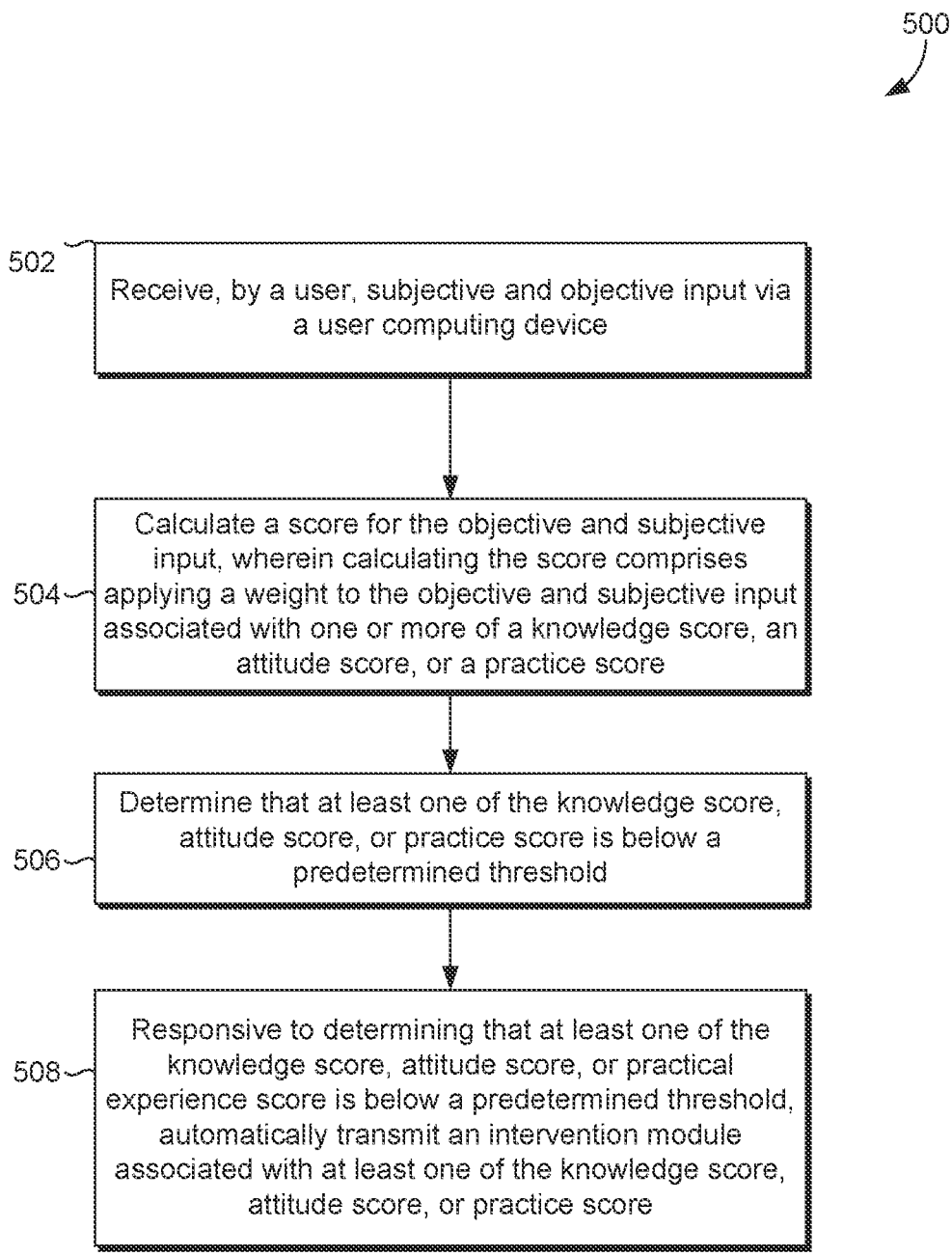
FIG. 5 illustrates a flow diagram of another method for providing objective electronic medical record (EMR) system adoption analysis, in accordance with an embodiment of the present disclosure.

Turning to FIG. 5, a flow diagram of an additional method for providing objective electronic medical record (EMR) system adoption analysis is illustrated. An example embodiment of this is comprised of one or more non-transitory computer-storage media having computer-executable instructions embodied thereon that, when executed, perform a method of providing objective electronic medical record (EMR) system adoption analysis. At step 502, the method comprises receiving a subjective input and an objective input via a user computing device. In further embodiments, the subjective input is comprised of at least one or a user's knowledge of an EMR system, a user's attitude towards the EMR system, or a user's practice with the EMR system. In further embodiments, the objective input is comprised of demographic data related to the user. In example embodiments, the demographic data may be comprised of at least a facility associated with a user, a role associated with a user, an experience level of a user, and other demographic information. In further embodiments, the received objective and subjective input may be stored in a database.

At step 504, the method further comprises calculating a score for the objective and subjective input, wherein calculating the score comprises applying a weight to the objective and subjective input associated with one or more of a knowledge score, an attitude score, or a practice score. In example embodiments, the weight applied to the objective and subjective data may be predetermined by a user. Additionally, the weight applied to the objective data and subjective data may be different, and the weight applied to each instance of objective data or each instance of subjective data may be different. For example, a higher weight may be applied to the objective input associated with the role of a user. Meaning that if a user has the role of doctor, a higher weight may be applied to the input associated with the role. This may also trigger certain subjective input to have higher weights. For example, a role of doctor may increase the weights applied to the subjective inputs associated with the knowledge of the EMR system as it may be more important for a user associated with the role doctor to have a higher knowledge of the EMR system. In further embodiments, this increased weight based on the role of doctor means that the user needs to incorrectly answer fewer questions associated with knowledge in order to fall below a threshold.

In further embodiments, a different weight may be applied to the different categories of subjective input wherein the different categories are associated with a user's knowledge of the EMR system, a user's attitude towards the EMR system, or a user's practice with the EMR system. In example embodiments, different weights may be applied to different categories based on the demographic data associated with type of facility, or years of experience. For example, inputting certain demographic data may trigger one or more categories of subjective input to have higher or lower weights applied to them. In further embodiments, different weights may be applied to the objective or subjective input based on the number of times the subjective or objective input have been received for a user. For example, if the system receives a subjective input and an objective input from a user more than once, and each time, it is determined that the system is not up to date, the weights applied to the input for this particular user may be progressively increased. For example, this could be described as the user failing an assessment by requiring the update to be caused. Therefore, future assessments may be weighted differently accounting for the fact that the particular user more often than not has a system that is not up to date.

At step 506, it is determined that at least one of the knowledge score, attitude score, or practice score is below at least one predetermined threshold. In further embodiments, the calculated score, weights applied to the different inputs, the objective inputs, the subjective inputs, or the user may be stored in a database associated with the EMR system. In further embodiments, the data stored in this database may be retrieved prior to retrieving new subjective input and objective input from the user associated with the stored data. Therefore, the weights and received inputs may change based on the stored data. In further embodiments, the at least one predetermined threshold may be different for each of the categories of knowledge, attitude, or practice. Additionally, at least one predetermined threshold may be the same for each of the categories. In further embodiments, the at least one predetermined threshold may be customized for different users. For example, if it is determined that a user's score in each category is consistently higher than the threshold, then the threshold may be maintained or lowered, meaning that it is harder to fall below the threshold. If it is determined that a user regularly scores below the threshold in one or more categories, the at least one predetermined threshold may be increased meaning that it is easier to fall below the threshold. These examples show that the score may be flexible to take into account a user who needs constant assistance versus a user that consistently has appropriate knowledge, attitude and practice.

At step 508, responsive to determining that at least one of the knowledge score, attitude score, or practice score is below at least one predetermined threshold, a retraining module associated with at least one if the knowledge score, attitude score, or practice score is automatically transmitted to the user. In example embodiments, the retraining module associated with the knowledge score is configured to reeducate the user regarding aspects of the EMR system by providing information related to the EMR system. The retraining module associated with the attitude score may be configured to educate the user regarding the importance of using the EMR system. And, the retraining module associated with the practical use score is configured to educate the user regarding how to properly use the EMR system.

In example embodiments, the retraining modules may be comprised of education curriculums designed to reeducate the user in relation to the score which fell below the threshold. This curriculum may include calendar notifications related to meetings with supervisors or education teams, educational documents or videos, or additional practice questions. Each retraining module is designed to increase the score associated with at least one of knowledge, attitude or practice. For example, the retraining module associated with the knowledge score may contain specific information regarding the EMR system. This may include text documents or figures designed to make a user better understand how to use the EMR system and issues that may arise while using an EMR system.

An example intervention module may comprise retraining on using the EMR and associated with attitude may contain data as to the effectiveness and efficiency of an EMR system. Additionally, it may include statistics showing that EMR systems allow more patients to be seen and cared for, or statistics showing how EMR systems reduce opportunities for errors. This retraining module may include any information that can assist a user in understanding the reason that an EMR system is used. An example retraining module associated with practice may include videos or diagrams which show a user how to properly use an EMR system. It may also include information related to which roles input which types of information into an EMR system and at what times an EMR system should be used. This retraining module is designed to help a user better understand exactly how an EMR system is to be used and by whom it is to be used.

Figure 6:
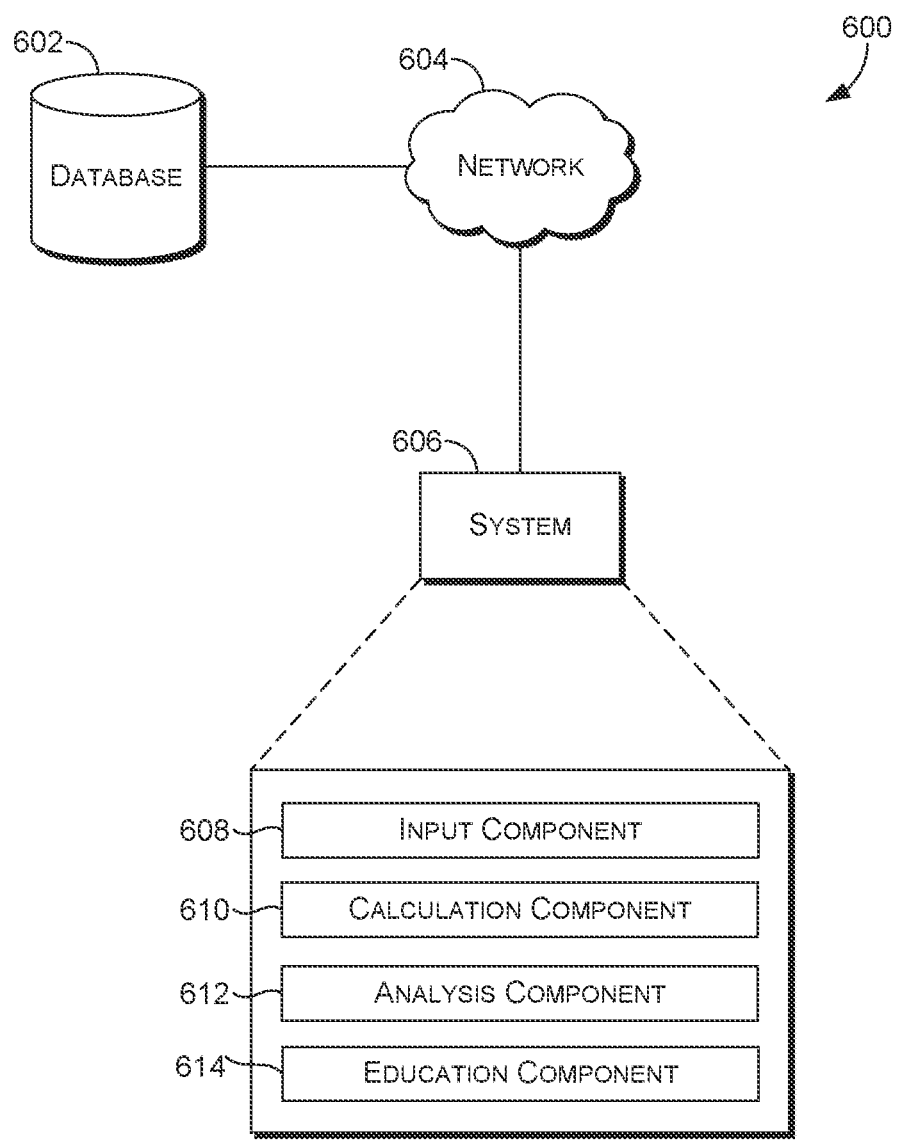
FIG. 6 illustrates a block diagram of an objective electronic medical record (EMR) system adoption analysis system environment, in accordance with an embodiment of the present disclosure.

Turning to FIG. 6, a block diagram of an objective electronic medical record (EMR) system adoption analysis system environment is illustrated. In embodiments, the system environment is comprised of a database 602, a network 604, and a system 606. The system may be comprised of a hardware processor configured to perform operations in response to receiving an instruction selected from a predefined naïve instruction set of codes, and a memory. The system may be further comprised of an input component 608 configured to receive, by a user, a subjective input and an objective input via a user computing device. The subjective input may be comprised of at least one of a knowledge assessment related to an EMR system, an attitude assessment related to the EMR system, or a practice assessment related to the EMR system. Additionally, the objective input may be comprised of demographic data related to the user. In further embodiments, the subjective input and the objective input is received in association with displayed questions, an example of which is illustrated in FIG. 9.

The system further comprises a calculation component 610, configured to calculate a score for the objective and subjective input. In further embodiments, calculating the score comprises applying a weight to the objective and the subjective input to determine one or more of a knowledge score, an attitude score, or a practice score. The system further comprises an analysis component 612 configured to determine that at least one of the knowledge score, attitude score, or practice score is below at least one predetermined threshold. The system further comprises an education component 613 configured to, responsive to determining that at least one of the knowledge score, attitude score, or practice score is below the at least predetermined threshold, automatically transmit, to the user, a retraining module associated with at least one of the knowledge score, attitude score, or practice score. In example embodiments, the transmitted retraining module, the subjective input, and the objective input, are stored in a database associated with the user. In further embodiments, the system further comprises a display component configured to cause display of a notification on a graphical user interface associated with a second user's computing device stating that the retraining module has been transmitted to the user.

Turning to FIG. 7, an exemplary scoring system for the objective electronic medical record (EMR) system adoption analysis is illustrated. As will be understood herein, receiving the objective and subjective input, scoring the inputs, and determining that the EMR system has not been downloaded, may be described as an Assessment. Additionally, the determined score may be described as the CLEAR Score. In further embodiments, the CLEAR Score may be determined based on values attributed to the objective and subjective input based on a response key. The response key may contain predetermined weights and correct or incorrect answers or ranges for answers. In example embodiments, the Assessment is provided to a user who in response provided the requested objective and subjective input. A CLEAR Score is determined based on the input, and based on the Score, an intervention or remedy may be implemented. Once the intervention or remedy has been implemented, a new Assessment may be provided to the user who, in response, provides the requested objective and subjective inputs. The Assessment is then scored taking into account the user's previously received CLEAR Score. This can continue at regular intervals, or until a desired CLEAR Score is reached.

In further embodiments, the Assessment may be administered across an entire healthcare facility, with regard to a particular EMR system component, or across a healthcare role, wherein the healthcare role can be comprised of doctor, nurse, medical assistant, etc. The CLEAR Score in these embodiments may be determined for the entire role, facility, or regarding the use of a particular component. In example embodiments, this group CLEAR Score may be determined with each user weighted the same across the scoring group, or particular users or types of users may be weighted more or less. Based on determining the group CLEAR Score, an intervention or remedy may be implemented across the entire group. In further embodiments, the scores, trends, and impact of the intervention across the entire group may be analyzed and stored in association with the group.

Figure 8:
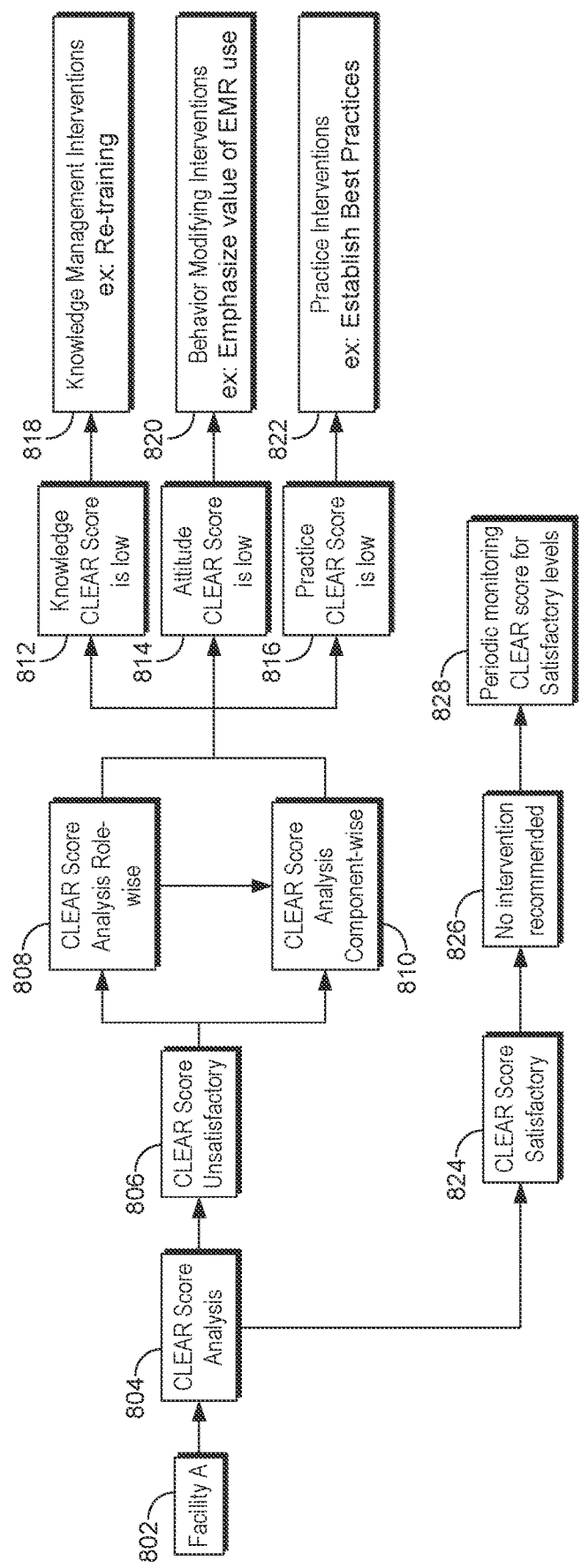
FIG. 8 illustrates a flow chart of an example assessment, scoring and intervention process, in accordance with an embodiment of the present disclosure.

Turning to FIG. 8, a flow chart of an example assessment, scoring, and intervention process is illustrated. It will be understood that this is one example of the implementation of the Assessment and CLEAR Score Analysis and intervention. Starting at block 802, a particular facility is determined to take the Assessment. Once the Assessment is taken, the CLEAR Score is analyzed at block 804. If the CLEAR Score is determined to be Satisfactory, the method moves on to block 824, if the CLEAR Score is determined to be unsatisfactory, the method moves to block 806. From block 824, the method includes no intervention recommendation 826, and then at block 828, the CLEAR Score for Facility A is periodically monitored.

Returning to a CLEAR Score which is unsatisfactory at block 806, the CLEAR Score may then be analyzed from a role-wise perspective at block 808, at a component-wise perspective at block 810, or at both perspectives. At block 808 and block 810, the CLEAR Score is analyzed to determine the CLEAR Score for three separate categories, namely knowledge, attitude, and practice. If the CLEAR Score associated with knowledge is low, the method continues to 812. If the CLEAR Score associated with attitude is low, the method continues to 814. And, if the CLEAR score for practice is low, the method continues to 816. When determining the CLEAR Score associated with each category, the categories may be associated with predetermined thresholds. If the score associated with a category is below a threshold, then it may be treated as low. Additionally, the method can continue to any combination of 812, 814, and 816. For example it may be determined that only the CLEAR Score associated with knowledge is low, or it may be determined that the CLEAR Score associated with each category is low.

Based on determining that at least the CLEAR Score associated with knowledge is low, the method continues to 818. At 818, a particular type of intervention is implemented associated with a low knowledge score. This can be described as a knowledge management intervention and one example intervention would be conducting EMR system re-training, to increase the users' knowledge of the EMR system. Based on determining that at least the CLEAR Score associated with attitude is low, the method continues to 820. At 820, a particular type of intervention is implemented associated with a low attitude score. This can be described as a behavior modifying intervention and one example intervention would be conducting training which emphasizes the value of EMR systems. Based on determining that at least the CLEAR Score associated with practice is low, the method continues to 822. At 820, a particular type of intervention is implemented associated with a low practice score. This can be described as a practice intervention and one example intervention would be conducting training which established best practices when using an EMR system.

Turning to FIG. 9, an example Assessment Questionnaire is illustrated. The Questionnaire illustrated in FIG. 9 may be displayed on a graphical user interface associated with a user. The user may then provide subjective inputs and objective inputs as described throughout the disclosure, in response to the displayed questions or prompts. In example embodiments, questions 1 through 10 may request demographic information objective inputs wherein the objective inputs are related to demographic information associated with a user. As can be seen in FIGS. 9A and 9B, the Questionnaire may contain questions associated with a role for a user, years of experience in a position, and in the healthcare position, among others. As described throughout the disclosure, these requested inputs may be supplemented with information gathered from metadata associated with the user, or with information in a database of an EMR system.

Moving to the second half of FIG. 9B, through 9F, a multitude of exemplary questions related to subjective input are displayed. In example embodiments, these questions may be related to at least the categories of knowledge, attitude, and practice. In the example embodiment illustrated in FIGS. 9A-9F, questions 11 through 18 represent questions associated with the knowledge category, questions 19A-19L represent questions associated with the attitude category, and questions 20A-20J represent questions associated with the practice category.

As can be seen by the example questions, the knowledge category questions are designed to test a user's knowledge of an EMR system, or an update associated with an EMR system. These questions can analyze how informed a user is as to the mechanics of an EMR system. By scoring low in this category, the analyzed score can for example determine that a user may not be aware of how to update, download, or use their EMR system. This can be an indication that the user has not downloaded the EMR system, that the user does not use the EMR system sufficiently, or does not know how to update their system. Also, as can be seen through the example questions, the attitude category questions are designed to test a user's attitude towards an EMR system. If a user scores low in this category, it can indicated that the user does not view EMR systems as important to the healthcare industry, or that they do not believe that it is necessary to update or download the systems as requested. Finally, as can be seen through the example questions, the practice category questions are designed to test a user's practice with an EMR system as well as their knowledge as to who uses it for what reason, and how often it should be used. By scoring low in this category, it may indicate that the user has not downloaded, does not use, or has not updated the EMR system often enough, it can also indicate that they are using the EMR system improperly.

In example embodiments, once the questionnaire answers have been received from the user via a graphical user interface, the answers are automatically checked against a key, and the predetermined weights are applied to the different categories. This may be supplemented by objective input which is retrieved from metadata associated with a user, or from a database associated with the EMR system. In example embodiments, the results of the scoring analysis are used to determine if the EMR system has been downloaded, is up to date, or being used appropriately.

The present invention has been described in relation to particular embodiments, which are intended in all respects to be illustrative rather than restrictive. Further, the present invention is not limited to these embodiments, but variations and modifications may be made without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations.

The invention claimed is:

1. One or more non-transitory computer-storage media having computer-executable instructions embodied thereon for performing a method of providing objective electronic medical record (EMR) system adoption analysis that, when executed by a computer system cause the computer system to:

train a natural language processing model to allocate subjective inputs into categories of knowledge of the EMR system, attitude towards the EMR system, and practice with the EMR system based on the subjective inputs and objective inputs;

for a group of users associated with a healthcare facility, display, in a graphical user interface of a computing device associated with a user, questions that prompt the user to provide a subjective input;

receive, at a server device through a network, the subjective input from the computing devices associated with the group of users and an objective input that comprises demographic data related to the group of users that includes at least roles of the group of users;

execute the trained natural language processing model by the server device to choose, based on the subjective inputs by individual users of the group of users and the objective inputs associated with the individual users, from among the categories of knowledge of the EMR system, attitude toward the EMR system, and practice with the EMR system into which to place one or more of the subjective inputs by the individual users;

calculate, by the server device, an attitude score for the healthcare facility based on checking the objective inputs and the subjective inputs that were placed into the category of attitude towards the EMR system by the trained natural language processing model against predetermined ranges in a key, wherein calculating the attitude score comprises applying to individual attitude scores for the group of users a first weight based on the role of the user and a second weight based on previous input by the user;

determine, by the server device, that the attitude score is below a predetermined threshold, wherein the attitude score is based at least in part on the subjective input that indicates a description by the user about an importance of the electronic medical record system; and responsive to determining that the attitude score is below the predetermined threshold, automatically transmit by the server device over the network to the computing devices of the group of users associated with the healthcare facility, a retraining module configured to automatically initiate, on the user computing device, an action to launch a video player to play a video associated with increasing the attitude score.

2. The media of claim 1, wherein an additional retraining module associated with a knowledge score is configured to reeducate the group of users regarding aspects of the EMR system by providing information related to the EMR system.

3. The media of claim 1, wherein an additional retraining module associated with a practice score is configured to provide the group of users with methods regarding how to properly use the EMR system.

4. The media of claim 1, wherein the retraining module associated with the attitude score is configured to educate the group of users regarding importance of using the EMR system.

5. The media of claim 1, wherein the objective input and the subjective input received from the group of users is stored in a database associated with the EMR system.

6. A system for providing objective electronic medical record (EMR) system adoption analysis, the system comprising:

a hardware processor configured to perform operations in response to receiving an instruction selected from a predefined native instructions set of codes;

a memory;

graphical user interfaces configured to, for a group of users associated with a healthcare facility, display in a computing device associated with a user, questions that prompt the user to provide a subjective input;

an input component configured to receive, at a server device through a network, the subjective input from the computing devices associated with the group of users and an objective input that comprises demographic data related to the group of users of the EMR system that includes at least roles of the group of users;

a natural language processing model that is (i) trained to allocate, by the server device, subjective inputs into one or more of a category of knowledge of the EMR system, a category of attitude towards the EMR system, and a category of practice with the EMR system based on subjective and objective inputs, and (ii) configured to, by the server device, based on the subjective inputs by individual users of the group of users and the objective inputs associated with the individual users, choose from among the categories of knowledge of the EMR system, attitude toward the EMR system, and practice with the EMR system into which to place one or more of the subjective inputs by the individual users;

a calculation component configured to calculate, by the server device, an attitude score for the healthcare facility based on checking the objective inputs and the subjective inputs that were placed into the category of attitude towards the EMR system by the trained natural language processing model against predetermined ranges in a key, wherein calculating the attitude score comprises applying to individual attitude scores for the group of users a first weight based on the role of the user and a second weight based on previous input by the user;

an analysis component configured to determine, by the server device, that the attitude score is below a predetermined threshold, wherein the attitude score is based at least in part on the subjective input that indicates a description by the user about an importance of the electronic medical record system; and an education component configured to, responsive to determining that the attitude score is below the predetermined threshold, automatically transmit, by the server device over the network to the computing devices of the group of users associated with the healthcare facility, a retraining module configured to launch a video player on the computing devices to play a video associated with increasing the attitude score.

7. The system of claim 6, wherein the retraining module, the subjective input, and the objective input, are stored in a database in association with the group of users.

8. The system of claim 6, wherein the subjective inputs are received in association with displayed questions.

9. The system of claim 6, wherein the system further comprises: a display component configured to cause display of a notification on a graphical user interface associated with a second user's computing device stating that the retraining module has been transmitted to the group of users.

10. A computer-implemented method for providing objective electronic medical record (EMR) system adoption analysis, the method comprising:

training a natural language processing model to allocate subjective inputs among a category of knowledge of the EMR system, a category of attitude toward the EMR system, and a category of practice with the EMR system based on the subjective inputs and objective inputs;

for a group of users associated with a healthcare facility, displaying, in a graphical user interface of a computing device associated with a user, questions that prompt the user to provide a subjective input;

receiving, at a server device through a network, the subjective input from the computing devices associated with the group of users that comprises demographic data related to the group of users that includes at least roles of the group of users;

execute the trained natural language processing model by the server device to choose, based on the subjective inputs by individual users of the group of users and the objective inputs associated with the individual users, from among the categories of knowledge of the EMR system, attitude toward the EMR system, and practice with the EMR system into which to place one or more of the subjective inputs by the individual users;

calculating, by the server device, an attitude score for the healthcare facility based on checking the objective inputs and the subjective inputs that were categorized into the category of attitude toward the EMR system by the trained natural language processing model against pre-determined ranges in a key, wherein calculating the attitude score comprises applying to individual attitude scores for the group of users a first weight based on the role of the user and a second weight based on previous input by the user;

determining, by the server device, that the attitude score is below a predetermined threshold;

based on determining that the attitude score is below at least one predetermined threshold, determining that the users have not adopted the EMR system; and responsive to determining that the user has not adopted the EMR system, automatically transmitting by the server device over the network to the computing devices of the group of users associated with the healthcare facility, a retraining module associated with the attitude score that is configured to launch a video player on the computing devices to play a video associated with increasing the attitude score.

11. The method of claim 10, further comprising adjusting weights applied to the individual attitude scores based on at least one of an age, or facility associated with an individual user of the group of users.

12. The method of claim 10, wherein the retraining module further comprises education material related to updating EMR systems.

13. The method of claim 10, wherein the retraining module, the subjective inputs, and the objective inputs, are stored in a database in association with an individual user of the group of users.

14. The method of claim 10, wherein the subjective inputs are received in association with displayed questions.

15. The method of claim 10, wherein the method further comprises causing display of a notification on a second user's computing device notifying that the retraining module has been transmitted.

16. The method of claim 10, wherein an additional retraining module associated with a knowledge score is configured to reeducate the group of users regarding aspects of the EMR system by providing information related to the EMR system.

17. The method of claim 10, wherein an additional retraining module associated with a practice score is configured to provide the group of users with methods regarding how to properly use the EMR system.

18. The method of claim 10, wherein the retraining module associated with the attitude score is configured to educate the group of users regarding importance of using the EMR system.

19. The method of claim 10, further comprising:
for the group of users, (i) a knowledge score for the healthcare facility based on the subjective inputs of the individual users that were categorized into the category of knowledge of the EMR system by the natural language processing model and (ii) a practice score for the healthcare facility based on the subjective inputs of the individual users that were categorized into the category of practice with the EMR system by the natural language processing model, wherein the attitude score was calculated based on the subjective inputs of the individual users that were categorized into the category of attitude toward the EMR system by the natural language processing model;

responsive to a determination by the server device that the knowledge score is below a predetermined threshold for the knowledge score, automatically transmitting by the server device over the network to the computing devices of the group of users associated with the healthcare facility a knowledge retraining module associated with the knowledge score that is configured to launch, on the computing devices, a video associated with increasing the knowledge score; and responsive to a determination by the server device that the practice score is below a predetermined threshold for the practice score, automatically transmitting by the server device over the network to the computing devices of the group of users associated with the healthcare facility a practice retraining module associated with the practice score that is configured to launch, on the computing devices, a video associated with increasing the practice score.

20. The method of claim 10, further comprising progressively increasing the second weight when the user has failed to update the EMR system.

\* \* \* \* \*